(12) United States Patent
Corcos et al.

(10) Patent No.: US 7,691,092 B2
(45) Date of Patent: Apr. 6, 2010

(54) AMBULATORY DEVICE FOR MEASURING URINE FLOW

(75) Inventors: Jacques Corcos, Ile Des Soeurs (CA); Jules Gauthier, Laval (CA); Ke Wu, Montreal (CA)

(73) Assignee: McGill University, Montreal (CA)

( * ) Notice: Subject to any disclaimer, the term of this patent is extended or adjusted under 35 U.S.C. 154(b) by 365 days.

(21) Appl. No.: 11/124,385

(22) Filed: May 9, 2005

(65) Prior Publication Data

US 2005/0288608 A1 Dec. 29, 2005

Related U.S. Application Data

(60) Provisional application No. 60/568,667, filed on May 7, 2004.

(51) Int. Cl.
*A61M 1/00* (2006.01)
*A47K 11/00* (2006.01)

(52) U.S. Cl. .................. 604/318; 604/317; 4/144.1

(58) Field of Classification Search ......... 604/317–319; 4/144.1, 144.2; 16/110.1, 113.1, 408–410; 190/105, 115
See application file for complete search history.

(56) References Cited

U.S. PATENT DOCUMENTS

| | | | |
|---|---|---|---|
| 3,527,469 A * | 9/1970 | Gobin | ................. 280/655.1 |
| 4,066,414 A | 1/1978 | Selby | |
| 4,074,562 A | 2/1978 | North | |
| 4,291,692 A | 9/1981 | Bowman et al. | |
| 4,343,316 A | 8/1982 | Jespersen | |
| 4,554,687 A | 11/1985 | Carter et al. | |
| 4,589,280 A | 5/1986 | Carter | |
| 4,683,748 A * | 8/1987 | Carter | .................. 73/226 |
| 4,732,160 A | 3/1988 | Ask et al. | |
| 4,775,072 A * | 10/1988 | Lundblade et al. | .......... 220/766 |
| 4,891,993 A * | 1/1990 | Barker | ................. 73/863.52 |
| 5,078,012 A | 1/1992 | Ding et al. | |
| 5,176,148 A | 1/1993 | Wiest et al. | |
| 5,377,101 A | 12/1994 | Rollema | |

(Continued)

FOREIGN PATENT DOCUMENTS

EP 0 038 783 10/1981

(Continued)

OTHER PUBLICATIONS

PCK Electronic Industry and Trade Co. Ltd, New Flow Uroflowmeter—publicity.

*Primary Examiner*—Melanie J Hand
(74) *Attorney, Agent, or Firm*—Goudreau Gage Dubuc; Gwendoline Bruneau

(57) ABSTRACT

An ambulatory device for measuring urine flow comprises a portable hand-held container and a handgrip mounted thereto. A flow-measuring device is located in the container, and a means for collecting the data measured by the flow-measuring device is also provided. The parameters of the urine flow in the container are measured by the flow-measuring device and are processed by the aforementioned means for collecting data. The handgrip is pivotally mounted to the container by a double-pivot mechanism for maintaining the container substantially vertical in a number of positions of the handgrip. The flow-measuring device includes a sensor that measures a displacement of an air column related to a variation of pressure due to a variation of a urine level in the container.

14 Claims, 3 Drawing Sheets

U.S. PATENT DOCUMENTS

| | | |
|---|---|---|
| 5,807,278 A | 9/1998 | McRae |
| 5,891,051 A * | 4/1999 | Han et al. .................... 600/573 |
| 6,261,276 B1 * | 7/2001 | Reitsma ....................... 604/319 |
| 2003/0132079 A1 * | 7/2003 | Bellini ......................... 190/115 |

FOREIGN PATENT DOCUMENTS

| | | |
|---|---|---|
| EP | 0 608 593 | 8/1994 |
| EP | 1 260 240 | 11/2002 |
| WO | WO 84/03824 | 10/1984 |
| WO | WO 90/03149 | 4/1990 |
| WO | WO 93/16638 | 9/1993 |
| WO | WO 95/13016 | 5/1995 |

* cited by examiner

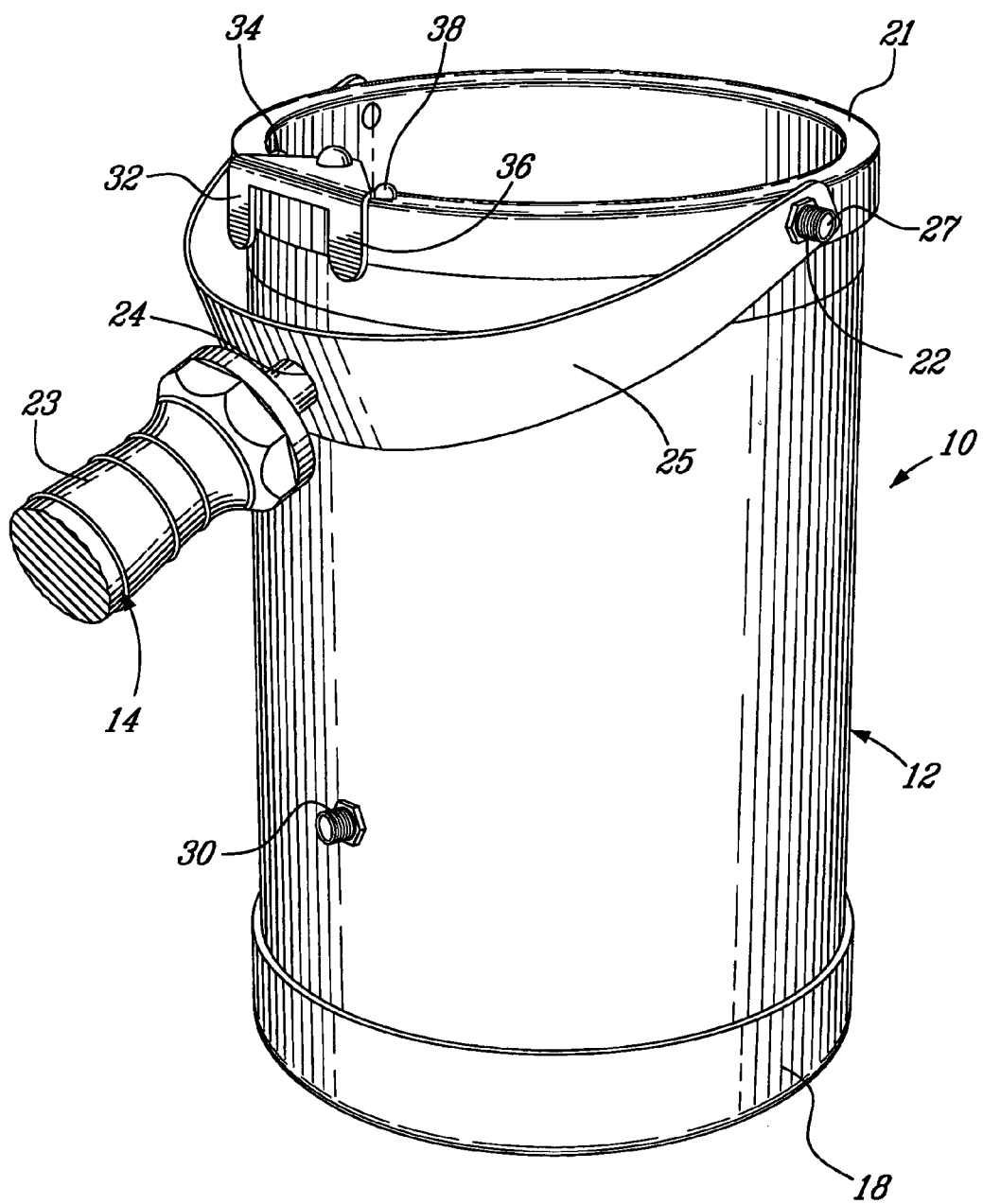

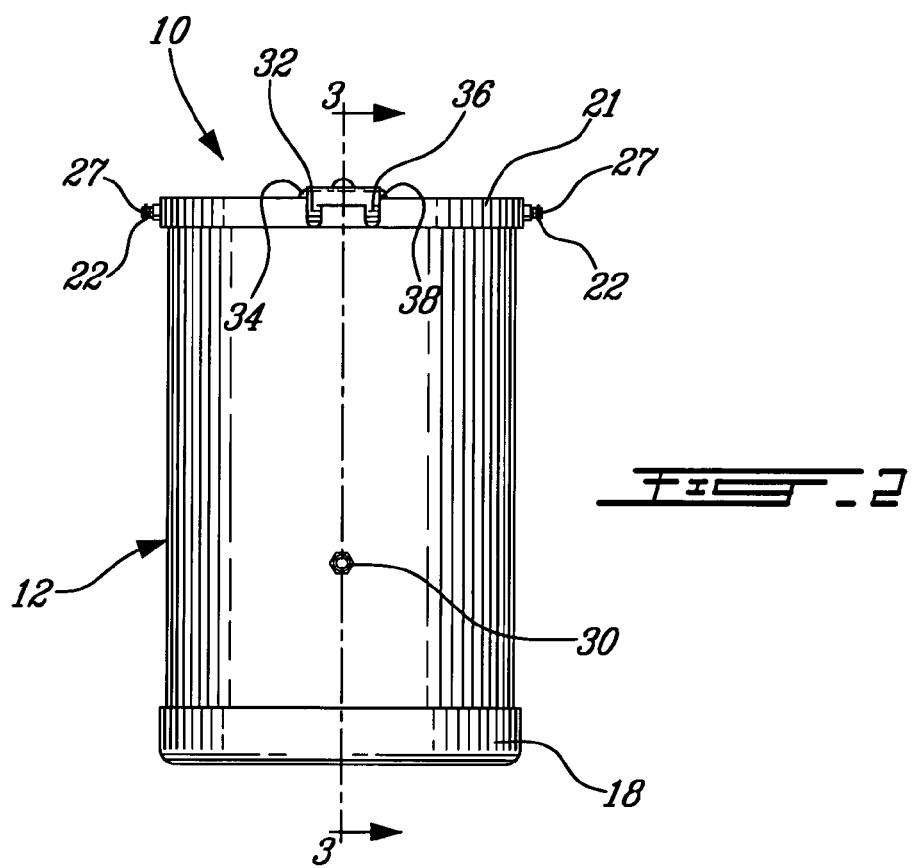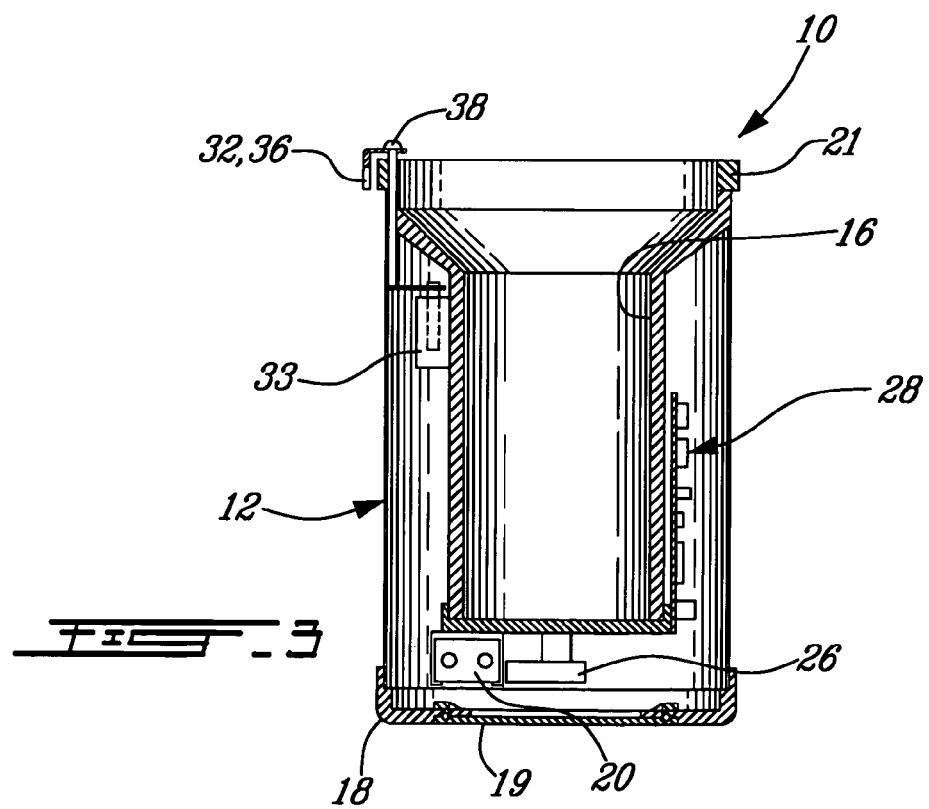

AMBULATORY DEVICE FOR MEASURING URINE FLOW

CROSS REFERENCE TO RELATED APPLICATIONS

This Application claims priority on U.S. Provisional Application No. 60/568,667, filed on May 7, 2004, which is herein incorporated by reference.

FIELD OF THE INVENTION

The present invention relates to flow measurements. More specifically, the present invention is concerned with a device for measuring urine flow.

BACKGROUND OF THE INVENTION

Flow measurement is an important tool in medical diagnostic procedures, for example, in urology matters. In such measurements, the urinary output of a patient is monitored as a means to study operation of the patients bladder and urethral dysfunctions or obstructions for example.

It has been shown that measuring the urinary output of patients in an ambulatory manner, the patients being out of the hospital and ideally at home, yields results that are most representative of the reality of the patients and of their daily life, unaltered by any stress that may be caused by being confined in an institutional environment such as an hospital for example.

A number of uroflowmeters are known in the art. For example, West et al., U.S. Pat. No. 5,176,148, disclose an uroflowmeter comprising a container supporting a measuring head, which includes a funnel leading to an intake chamber. The intake chamber communicates by a bottom part thereof to a first chamber containing a pressure measuring tube and to a second chamber connected at a top hereof to a first pressure sensor of a pressure sensor unit, in such a way that a lower edge of a vertical slot of the pressure measuring tube, of the intake chamber and of the second chamber are located in a common horizontal plane. A measuring tube extending from the measuring head to the container in a direction parallel to the pressure measuring tube, is connected to a second pressure sensor of the pressure sensor unit. The second pressure senior measures a filling height of urine in the container via an air column in the measuring tube, while the first pressure sensor measures a column height in the intake chamber via an air column in the second chamber, which allows to obtain, on the basis on an outflow of urine through the pressure measuring tube, the flow of urine.

Jespersen, in U.S. Pat. No. 4,343,316, describes an uroflowmeter comprising a volumetric calibrated container receiving an inlet tube, itself connected upstream to a catheter, and connected to a urine drainage bag by an outlet tube. The volumetric calibrated container has a double cone shape so as to allow for an amount of vertical misalignment thereof. An optical sensor allows visually monitoring a building up of urine into the container, thereby yielding a flow per unit time, and dumping thereof into the urine drainage bag.

Carter et al., in U.S. Pat. No. 4,554,687, teach a toilet-mounted uroflowmeter comprising a container fitting into a toilet bowl, and which is connected to a pressure sensor by a tube. A height of fluid in the container is associated with an air pressure sent to the pressure sensor by a tube, and thereby to a flow rate in the container.

In spite of these technological efforts, currently available uroflowmeters are bulky devices and establishing micturition calendars remains a mainly manual task, inherently prone to errors.

Therefore, there is a need in the art for an ambulatory device for measuring urine flow, which is easy to use by a patient and in a way that permits accuracy of results and a full processing of individual variations related to a given patient as well as an historical tracking of the patients urinary activities for establishing micturition calendars.

SUMMARY OF THE INVENTION

More specifically, in accordance with the present invention, there is provided an ambulatory device for measuring urine flow, comprising a portable hand-held container; a flow-measuring device located in said container; and a means for collecting data measured by said flow-measuring device; wherein parameters of the urine flow in said container are measured by said flow-measuring device and processed by said means for collecting data.

Also in accordance with the present invention, there is provided method for measuring urine flow, comprising the steps of: (a) providing an ambulatory device having a urine-receiving container, urine flow-measuring means and a means for collecting data measured by said flow-measuring means; (b) having a patient to urinate in said container; and (t) measuring parameters of the urine flow.

Other objects, advantages and features of the present invention will become more apparent upon reading of the following non-restrictive description of embodiments thereof, given by way of example only with reference to the accompanying drawings.

DESCRIPTION OF THE DRAWINGS

Reference will row be made to the accompanying drawings, showing by way of illustration an illustrative embodiment of the present invention, and in which:

FIG. 1 is a perspective view of an ambulatory device for measuring urine flow according to an embodiment of the present invention;

FIG. 2 is a side view of a container of the ambulatory device of FIG. 1, but without a handgrip assembly thereof;

FIG. 3 is a cross section of the container taken along line 3-3 of FIG. 2;

DESCRIPTION OF EMBODIMENTS OF THE INVENTION

Figure 4:
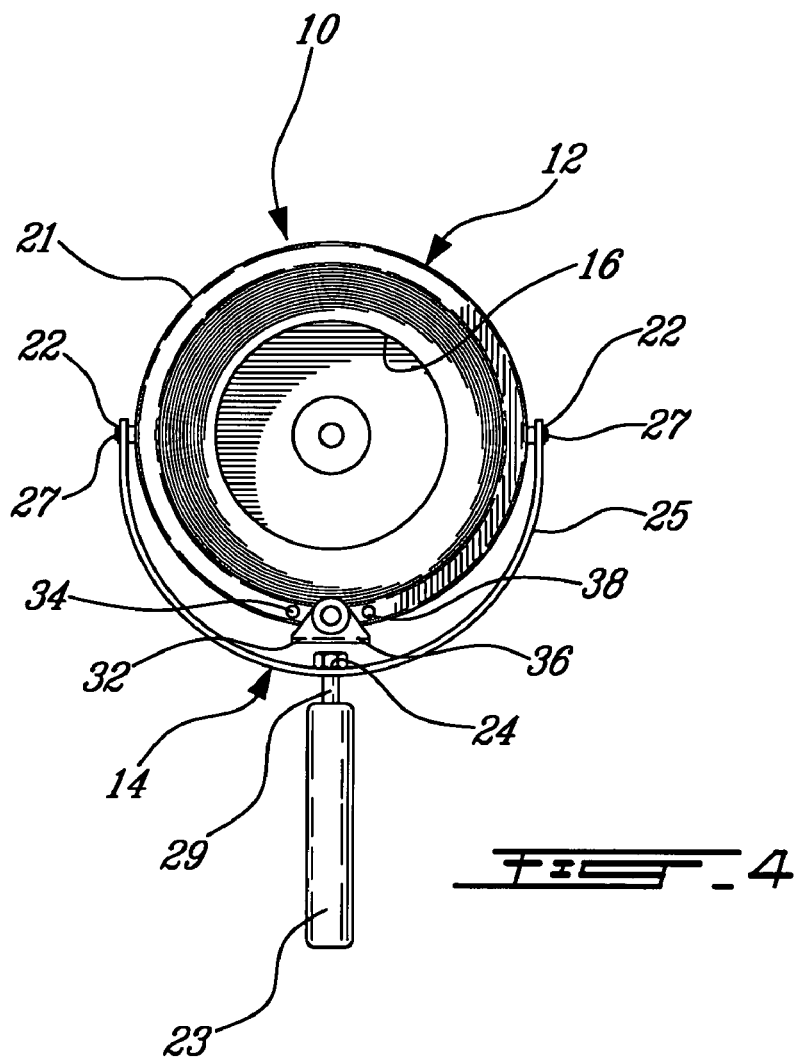
FIG. 4 is a top plan view of the ambulatory device of FIG. 1.
Figure 5:
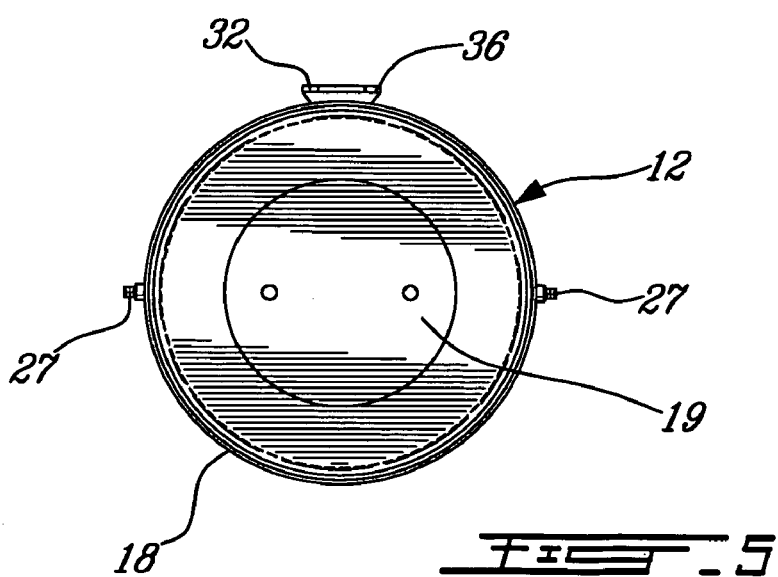
FIG. 5 is a bottom plan view of the container of FIG. 2.

There is provided an ambulatory device for measuring urine flow, which allows achieving measurement of a flow rate of urine in real time in a non intrusive and non invasive way, and establishing a micturition calendar, without any human intervention besides a patient urinating.

Turning to the figures of the appended drawings, an ambulatory device for measuring urine flow according to an embodiment of the present invention will be described.

The ambulatory device 10 comprises a container 12 provided with a handgrip assembly 14.

The container 12 is of a generally cylindrical shape as illustrated, and has an inside volume capacity typically of at least 600 ml. Inside surface walls of the container 12 are made of a material that is compatible with receiving urine and that is easily washable. For example, the container 12 may receive a removable inner receptacle 16, as shown in FIG. 3, which may, or not, be disposable. The container 12 further comprises a removable base 18 that may be provided with a removable cover 19 for allowing access to batteries 20.

The handgrip assembly 14 is removably mounted to an upper edge 21 of the container 12 by a double-pivot fastening mechanism comprising opposed first pivots 22 and a second pivot 24. The two pivots 22 are coaxial and extend perpendicularly to, and coplanarly with the second pivot 24.

More particularly, the handgrip assembly 14 includes a floating handle 23, an arcuate bracket 25 and a connector 29 therebetween. The first pivots 22 are herein constituted by a pair of fixed pins 27 that extend radially outwardly from the upper edge 21 of the container 12 and that engage openings (not shown) defined in the free ends of the bracket 25. The second pivot 24 allows the handle 23 to freely rotate along a longitudinal axis thereof with respect to the bracket 25. This can be achieved in a variety of ways, including having the connector 29 fixed to the handle 23 and rotatably extending through an opening defined in the central part of the bracket 25 such that the handle 23 (and the connector 29) can rotate about its longitudinal a and relative to the bracket 25. Alternatively, the connector 29 can be securely mounted to the bracket 25 while being rotatably journaled within the handle 23 thereby allowing the latter to rotate relative to the connector 29 (which extends within the handle 23) and to the bracket 25.

This double-pivot fastening mechanism 22 and 24 thus allows the container 12 to be maintained in a vertical position at all time independently of the way a patient is gripping the handle 23 while using the device 10 (see FIGS. 1 and 4). Such a handgrip assembly 14 is thereby suitable for both left-handed and right-handed persons.

Moreover, the handgrip assembly 14 may be easily removed from the container 12 by disengaging the first pivots 22, that is by disconnecting the arcuate bracket 25 from the fixed pins 27 provided on the upper edge 21 of the container 12, thereby allowing a compact storing of the device 10 for transportation for example. Typically, the arcuate bracket is spring biased into an engaged position onto the first pivots 22, such that it can be deployed outwardly, against its inherent spring force, for disengaging it from the first pivots 22.

A flow-measuring device 26 powered by the batteries 20 is located in a bottom inside part of the container 12 (see FIG. 3).

The flow-measuring device 25 may include a sensor that measures a displacement of an air column in response to a variation of pressure in the container 12 due to a variation of a liquid level in the container 12 as the patient urinates thereinto More precisely, the sensor measures a volume of liquid in the container 12 through a measure of a pressure therein, and therefore, provided that a time interval between the measures is known, allows calculating a flow rate.

The flow-measuring device 26 typically collects data at intervals, every other second for example, with an acquisition time of 200 seconds. The data are saved in a memory of an electronic circuit 28 included in the container 12 of the device 10 (see FIG. 3). Data collection may be stopped either by waiting 200 seconds or by emptying the container 12 following a sampling, both these actions resulting in peer being turned off from the device 10 thereby preventing undue discharge of the batteries 20.

The electronic circuit 28 may be connected to a peripheral equipment supporting a dedicated data processing program (not shown) through an output serial port 30 (e.g. a RS 232 connector) for allowing transmission of the data saved in the memory thereof to the peripheral equipment.

The peripheral equipment is typically a personal computer fitted with a corresponding input serial port. As people in the art will know, computers, such as some portable computers, which are not provided with such a serial port, may be upgraded by using PCMCA cards insertable into PCMCA port.

The electronic circuit 28 further supports an internal clock for saving an exact time of the sampling in terms of years, months, days, hours, minutes and seconds. The internal clock is programmed once a connection between the serial port 30 and the peripheral equipment is established, and then reset by pressing on a start button 32 (herein a toggle switch) of the device 10.

As any measuring device, the device 10 needs be calibrated. First, any prior calibration may be cancelled through the dedicated program of the peripheral equipment once the connection between the serial port 30 and the peripheral equipment is established. Then, communication between the device 10 and the peripheral equipment is triggered upon pressing on the start button 32 of the devise 10 and the calibration may take place as follows. First and second measurements are made respectively with the container 12 containing 500 ml of liquid and with the container 12 being empty. The two measurements are saved in the memory of the device 10 and then transferred to the peripheral equipment by prompting a start reading command of the dedicated program followed by pushing the start button 32. The dedicated program may comprise a visual interface displaying an advancement of the transfer as it is being performed. Once the transfer is over, a calibration command of the dedicated program is activated, which starts an assessment procedure of the two measurements before allowing the calibration to be saved one it is correct.

Obviously, this calibration step of the device 10 may be done by trained staff of the hospital prior to delivering the device 10 ready for use to the patient.

For starting a sampling, the device standing unconnected from any peripheral equipment, the patient actuates the start button 32 (which triggers a start switch 33) seen in FIG. 3), located on an upper edge of the container 12 as illustrated, or on the handgrip assembly 14 for example, which activates an operating indicator 34 (herein in the form of a pilot light), which remains activated during the sampling. The patient may indicate a degree of urgency of his/her need to urinate by pressing, for a predetermined length of time such as at least one second, on an urgency button 36 (herein a toggle switch), also placed in an accessible location, such that the readings of such an urgent urination are flagged bath respect to other readings resulting from "normal" urinations. The patient may be warned of a dysfunction of the device 10, such as low batteries, by an alert indicator 38 (herein in the form of a pilot light). During the sampling, data are collected by the flow-measuring device and saved in the memory of the devices.

At intervals, predetermined by the attending physician according to the autonomy of the memory of the device 10 and to an expected average use thereof by the patient, the device 10 is connected to a peripheral equipment supporting the dedicated program as described hereinabove for a transfer of the data. Once the transfer is over, the data may be saved in a file and may be visualized on a display under a number of forms well known in the art (tables, graphs etc.), as volume versus time and as flow rate versus time for a given sampling corresponding to the transferred data. Micturition calendars are therefore efficiently established.

People in the art will appreciate that since the container 12 is maintained in a vertical position at all time as described hereinabove, the liquid level is also maintained horizontal relative to the flow measuring device at all time, which results in an increased accuracy of measurements.

From the foregoing, it should now be apparent that the device of the present invention allows a control of the alignment of the device by the provision of the handgrip, a resulting ease of use and a resulting accuracy of measurements, as well as a reduced complexity due to a reduced number of parts and an absence of mobile parts.

Furthermore, the ambulatory uroflowmeter of the present invention allows establishing micturition calendars.

Although the present invention has been described hereinabove by way of embodiments thereof, it may be modified, without departing from the nature and teachings of the subject invention as described herein.

What is claimed is:

1. A handgrip assembly for an ambulatory device for measuring urine flow comprising a container housing a first chamber adapted for receiving urine and retaining the urine; and a second chamber adapted for receiving a flow-measuring device, said container being aligned in a vertical direction for ease of collection of the urine and accurate measurement of a variation of a liquid level in said first chamber independently of a grip of a user on said handgrip assembly comprising a handle, for the user to hold the container using a single hand as the user collects his urine in said container, and a bracket, said bracket being connected to said container by at least one radial pivot, said handle being connected to said bracket by a second pivot, said second pivot being perpendicular to said at least one radial pivot, said second pivot allowing a relative rotation of said handle relative to said bracket about a longitudinal axis of said handle and said at least one radial pivot allowing said container to pivot relative to said bracket.

2. An ambulatory device for measuring urine flow, remaining in a vertical direction whenever held by a handgrip assembly thereof, comprising a container housing a first chamber adapted for receiving urine and retaining the urine; and a second chamber adapted for receiving a flow-measuring device;

wherein said handgrip assembly comprises a handle, for a user to hold the container using a single hand as the user collects his urine in said container, and a bracket, said bracket being connected to said container by at least one radial pivot, said handle being connected to said bracket by a second pivot, said second pivot being perpendicular to said at least one radial pivot, thereby maintaining said container aligned in a vertical direction for ease of collection of the urine and accurate measurement of a variation of a liquid level in said first chamber independently of the grip of the user, said handle assembly comprising a connector between said handle and said bracket, said connector allowing a relative rotation of said handle relative to said bracket about a longitudinal axis of said handle.

3. The ambulatory device according to claim 2, wherein said connector is rotatably attached at a distal end thereof to said bracket via said second pivot and is fixedly attached at a proximal end thereof to said handle, whereby said handle and said connector can rotate relative to said bracket via said second pivot.

4. The ambulatory device according to claim 3, wherein said bracket is substantially arcuate and has opposed free ends attached to said upper end of said container via a pair of said radial pivots, said connector being rotatably attached to said arcuate bracket at a central portion thereof with said connector having at said distal end a pin journaled in a hole defined in said central portion of said arcuate bracket.

5. The ambulatory device according to claim 3, wherein said bracket is substantially arcuate and has opposed free ends attached to said upper end of said container via a pair of said radial pivots, said free ends defining openings engaged by a pair of pins extending outwardly from opposed sides of said upper end of said container.

6. The ambulatory device according to claim 1, wherein said first chamber is removable from said container.

7. The ambulatory device according to claim 1, wherein said container includes a removable cover at a base thereof for providing access to batteries of said ambulatory device.

8. The ambulatory device according to claim 1, wherein said flow-measuring device includes a sensor adapted for measuring a variation of pressure due to a variation of the urine level in said first chamber.

9. The ambulatory device according to claim 1, wherein an electronic circuit is provided in said container, said flow-measuring device being adapted to collect data that can be saved in a memory of said electronic circuit.

10. The ambulatory device according to claim 9, wherein said container includes an output connector for allowing data in said memory to be transmitted to a peripheral equipment, said data including at least one of urine volumes, urine flow rates and urine collection times.

11. The ambulatory device according to claim 9, wherein said electronic circuit includes a clock such that said data collected by said electronic circuit includes at least one of urine volumes, urine flow rates and urine collection times, whereby micturition calendars can be established by said peripheral equipment.

12. The ambulatory device according to claim 9, wherein a start button is provided to actuate said flow-measuring device.

13. The ambulatory device according to claim 12, wherein at least one luminous indicator is provided for indicating when said flow-measuring device is actuated.

14. The ambulatory device according to claim 9, wherein an urgency button is provided for indicating that an urgent urination is being received by said container.

\* \* \* \* \*

UNITED STATES PATENT AND TRADEMARK OFFICE
CERTIFICATE OF CORRECTION

PATENT NO.         : 7,691,092 B2                                          Page 1 of 1
APPLICATION NO.    : 11/124385
DATED              : April 6, 2010
INVENTOR(S)        : Jacques Corcos, Jules Gauthier and Ke Wu It is certified that error appears in the above-identified patent and that said Letters Patent is hereby corrected as shown below:

On the Title Pg, item (73) Assignee: insert below McGill University, Montreal (CA):
--Corporation de l'École Polytechnique de Montréal, Montréal (CA)--

Signed and Sealed this

First Day of June, 2010

David J. Kappos
*Director of the United States Patent and Trademark Office*